United States Patent [19]

D'Amore et al.

[11] Patent Number: 4,618,702
[45] Date of Patent: Oct. 21, 1986

[54] MANUFACTURE OF BUTANEDICARBOXYLIC ACID ESTERS

[75] Inventors: Michael B. D'Amore; Roger R. Ellefson, both of Wilmington, Del.

[73] Assignee: E. I. Du Pont de Nemours and Company, Wilmington, Del.

[21] Appl. No.: 694,679

[22] Filed: Jan. 24, 1985

[51] Int. Cl.$^4$ ............................................. C07C 67/38
[52] U.S. Cl. ..................................... 560/204; 502/20; 502/28; 502/152; 502/155; 502/326; 560/190; 560/207
[58] Field of Search ................. 560/204, 207, 190

[56] References Cited

U.S. PATENT DOCUMENTS

| | | | |
|---|---|---|---|
| 3,481,975 | 12/1969 | Rudkovsky et al. | 260/533 |
| 4,169,956 | 10/1979 | Kummer et al. | 560/204 |
| 4,171,451 | 10/1979 | Kummer et al. | 560/204 |
| 4,258,203 | 3/1981 | Platz et al. | 560/204 |
| 4,259,520 | 3/1981 | Kummer et al. | 560/204 |
| 4,310,686 | 1/1982 | Kummer et al. | 560/204 |

FOREIGN PATENT DOCUMENTS 1092694 11/1967 United Kingdom.

OTHER PUBLICATIONS

The Cobalt Carbonyl-Catalyzed Hydroesterification of Butadiene with Carbon Monoxide and Methanol, Akio Matsuda, Bulletin of the Chemical Society of Japan, vol. 46, 524–430 (1973).

Mechanistic Pathways in the Catalysis of Olefin Hydrocarboxylation by Rhodium, Iridium, and Cobalt Complexes, D. Forster et al., Catal. Rev.-Sci. Eng., 23(1&2) pp. 89–105 (1981).

Imyanitov et al., Karbonilirovanie Menasyshchennykh Uglevodorodov (1968) 225–32, 232–43, CA 71, 21648y–21649z (1969).

*Primary Examiner*—Natalie Trousof
*Assistant Examiner*—Vera C. Clarke

[57] ABSTRACT

Increased catalyst concentration relative to butadiene in its carboalkoxylation permits operation at reduced pressure and simplifies process steps.

7 Claims, No Drawings

MANUFACTURE OF BUTANEDICARBOXYLIC ACID ESTERS

BACKGROUND OF THE INVENTION

1. Field of the Invention

This invention relates to the manufacture of butanedicarboxylic acid esters by the cobalt catalyzed carboalkoxylation of butadiene in the presence of a nitrogen base and, more particularly, to the use of increased amounts of the cobalt catalyst relative to butadiene and base to permit operation at reduced pressure and to simplify the overall process.

2. Description of the Prior Art

The cobalt catalyzed carboalkoxylation of butadiene to produce dicarboxylic acid esters as the principal reaction products has been described in the literature. U.S. Pat. No. 4,169,956, issued on Oct. 2, 1979, describes a typical stepwise carbomethoxylation of butadiene initially to methylpentenoate and then to dimethyladipate employing pressures in the range 300-2000 atm and approximately 0.01-0.1 mole of cobalt per mole of butadiene.

U.S. Pat. No. 3,481,975, issued on Dec. 2, 1969, describes a process for preparing dicarboxylic acids in one step by reacting butadiene, carbon monoxide and water at a pressure of 430 atm using relatively large amounts of dicobalt octacarbonyl but the selectivity to adipic acid is low.

A general discussion of the hydroesterification of butadiene is contained in the article entitled *The Cobalt Carbonyl-Catalyzed Hydroesterification of Butadiene With Carbon Monoxide and Methanol*, Akio Matsuda, Bulletin of the Chemical Society of Japan, Vol. 46, 524-530 (1973). Hydrocarboxylations and hydroesterifications employing cobalt catalysts are discussed in the article *Mechanistic Pathways in the Catalysis of Olefin Hydrocarboxylation by Rhodium, Iridium, and Cobalt Complexes*, D. Forster et al., Catal. Rev. - Sci. Eng. 23(1&2) p. 89-105 (1981).

The preparation of the esters of 3-pentenoic acid using cobalt catalysts is disclosed in German Pat. No. DE 3040432, published on June 19, 1981. The production of 3-pentenoic acid is discussed in an articles by Imyanitov et al., Karbonilirovanie Nenasyshchennykh Uglevodorodov (1968) 225-32, 232-43, CA 71 21648y-21649z, a portion of which former disclosure appears in U.K. Pat. No. 1,092,694 published on Feb. 4, 1965. The reaction was studied in a pyridine solvent with cobalt carbonyl catalysts under a pressure of 120-500 atmospheres.

Variations in the reaction conditions employed for the carboalkoxylation are disclosed in U.S. Pat. Nos. 4,171,451, issued on Oct. 16, 1979; 4,310,686, issued on Jan. 12, 1982 and 4,258,203, issued on Mar. 24, 1981. U.S. Pat. No. 4,259,520, issued on Mar. 31, 1981 teaches that butadiene must be removed before the carboalkoxylation of the pentenoate.

SUMMARY OF THE INVENTION

A process for the carboalkoxylation of butadiene by reacting butadiene, carbon monoxide and at least one lower alkyl alcohol, e.g., methanol, which process comprises or consists essentially of introducing at least about 0.15, preferably 0.17-0.45 mole of a cobalt-containing catalyst based upon cobalt and at least 0.5, preferably 0.5-3.0 moles of nitrogen base, e.g., pyridine, per mole of butadiene along with the carbon monoxide, alcohol and butadiene into a reactor and thereafter reacting the butadiene at elevated temperature and pressure.

In one preferred embodiment the reaction is conducted in two steps with the liquid reaction medium from the first step of the carboalkoxylation, e.g., a solution of methyl pentenoate, cobalt catalyst, pyridine and minor amounts of unreacted butadiene is introduced into the second step with no removal of material from the solution.

DETAILED DESCRIPTION OF THE INVENTION

The carboalkoxylation reaction is advantageously conducted in a plurality of steps or stages initially involving the reaction of butadiene to form the alkylpentenoate and then the reaction of the pentenoate to form the dialkyladipate.

In the first step butadiene is reacted with carbon monoxide and a lower alkyl alcohol having 1-8, preferably 1-4 carbon atoms, e.g., methanol and cyclohexanol. Catalyst deactivation is roughly inversely proportional to the number of carbon atoms in the alcohol. Temperatures in the range 125°-140° C., preferably 130°-135° C., and pressures in the range 100-500 atm are employed. The amount of catalyst expressed as the molar ratio of catalyst to butadiene as introduced or fed is significantly higher than in processes of the prior art and is usually within the range of at least 0.15 and preferably 0.17-0.45 mole of cobalt-containing catalyst as cobalt per mole of butadiene. This higher level of catalyst permits a reduction in pressure for the first step of the carboalkoxylation while maintaining yield and reaction rates comparable to higher pressure operation using previously employed levels of catalyst. An additional advantage of the present invention is that the higher level of catalyst for this first step is not accompanied by an increase in or higher level of the nitrogen base. The result is that the nitrogen base to cobalt ratio in the reaction product from the first step of the carboalkoxylation is sufficiently close to the optimum for the second step that no adjustment in the reaction product is required to conduct the second step. Removal of nitrogen base as required by prior art processes before the commencement of the second step is thereby eliminated and since the previously required removal of base must be conducted under vacuum to avoid conditions conducive to rapid catalyst degradation, the present invention avoids that complicated, energy-consuming operation. Optionally minor amounts of unreacted butadiene normally present in the reaction product from the first step can be removed before steps, but since this separation is readily accomplished, e.g., by simple flashing, catalyst degradation is minimal.

However, it is within the purview of the present invention that all or some portion of the catalyst which is deactivated in the first step can be regenerated, e.g., by contact with a strong acid ion exchange resin, before the conduct of the second step. This regeneration, as in the case of butadiene removal, does not cause significant catalyst degradation.

The conditions employed in the second step, i.e., the carboalkoxylation of the alkylpentenoate to the dialkyladipate, are similar to those employed in the initial step according to the present invention except that lower pressures are permissible and higher, temperature is required, e.g., 140°-200° C.

The catalyst employed in the carboalkoxylation is a cobalt carbonyl compound preferably in combination with a tertiary nitrogen base. Sources of cobalt include finely divided metallic cobalt, inorganic salts such as cobalt nitrate or carbonate, organic salts, in particular carboxylates. Cobalt carbonyl or hydridocarbonyls can likewise be employed; dicobalt octacarbonyl is very suitable. Typically the cobalt-containing catalyst is prepared by dissolving a cobalt compound [typically as $Co_2(CO)_8$] in the nitrogen base and alcohol at room temperature under a nitrogen blanket whereupon the active catalyst forms in situ.

The tertiary nitrogen bases which are employed as promoters for the cobalt comprise N-heterocyclic compounds with 5-11 carbon atoms and a pKa in the range 4-8, preferably 5-7, and include, but are not necessarily limited to, pyridine (pKa 5.3), alkylpyridines, e.g., 3-picoline (pKa 6.0) and isoquinoline (pKa 5.4). Pyridine is the preferred nitrogen-containing base.

As mentioned hereinabove, the deactivated catalyst in the reaction product from either step can be regenerated by contacting the reaction product with any strong acid ion exchange resin including any of the known polymers in the macroporous or gel form which contain strongly acidic functional groups such as styrenedivinylbenzene copolymers substituted with sulfonic or phosphonic acid functional groups, particularly those macroporous resins sold under the trade names "Amberlyst 15" and "Dowex MSC-1" and gel resins sold under the trade names "Amberlite 118", "Duolite ES 26" and "Dowex HCR-S" are operable.

Resins of formaldehyde condensation polymers substituted with sulfonic acid groups, e.g., "Duolite C-3" are also useful. Considerations common in ion exchange technology, e.g., a holdup time, temperature, capacity of resin and concentration of species to be removed are applicable to this process. The ion exchange resin can be reactivated by contact with aqueous acid.

In a continuous process butadiene, carbon monoxide, an appropriate alcohol or mixture thereof and pyridine are introduced under pressure into an autoclave along with recycle catalyst obtained as described below. As the carboalkoxylation to the alkylpentenoate is completed, the reaction product is withdrawn and directed to a second reactor along with additional alcohol and, optionally, fresh catalyst where the butanedicarboxylic acid esters are formed at elevated temperatures relative to the first step. Water is contacted with the product from the second reactor to enhance removal of the ester via a hydrocarbon extraction. After separation from the hydrocarbon, the water and the nitrogen base are passed through a strong acid ion exchange resin to regenerate the catalyst complex. Water is removed before the regenerated catalyst and nitrogen base are recycled to the initial reactor. The diester is recovered from the hydrocarbon phase by known methods.

The following examples are presented to illustrate but not to restrict the present invention. Parts and percentages are by weight unless otherwise noted.

EXAMPLE 1

Approximately 22.2 g of dicobalt octacarbonyl were dissolved in 60 g of methanol and 70 g of pyridine added slowly to the resultant solution under an inert atmosphere at room temperature. The resulting solution along with 23.1 g of butadiene was charged to a 300 ml stirred stainless steel autoclave and the autoclave was pressurized to 176 atm with carbon monoxide. The contents of the autoclave were heated to 135° C. with stirring and maintained under such conditions for two hours following which a sample of the contents were removed and analyzed by gas chromatography. The analysis indicated a yield of methylpentenoate of 82.9% and a 98% conversion of butadiene.

The contents of the autoclave were cooled to room temperature and the autoclave then vented to the atmosphere to purge unreacted butadiene. The reactor was repressurized to 176 atm with carbon monoxide and the contents heated to 175° C. with stirring. These conditions were maintained for approximately four hours following which the contents of the autoclave were cooled to room temperature, recovered and analyzed. Analysis indicated a dimethyladipate yield of 53% and a 58% conversion of methylpentenoate.

EXAMPLE 2

Example 1 was repeated except that 22.9 g of butadiene were charged, the pressure was 272 atm, the temperature was 130° C., the first step was conducted for 1.5 hours and the reactor was not vented to the atmosphere between steps, i.e., the temperature of the contents of the reactor were increased immediately after a sample of the reaction product from the first step was obtained. Analysis indicated a yield of methylpentenoate of 85.8%, a conversion of butadiene of 97.0%, a yield to dimethyladipate of 57.0% and a conversion of methylpentenoate of 54.0%.

EXAMPLES 3-6

The first step of Example 1 was repeated except as noted in the Table where the amounts of reactants, the reaction conditions and the results are reported.

TABLE

| Example No. | Feed (gms) $Co_2(CO)_8$ | Feed (gms) Butadiene | Cobalt/Butadiene (mole ratio) | Time (Min) | Pressure (atm) | Temperature (°C.) | Yield of Methylpentenoate (%) | Conversion of Butadiene (%) |
|---|---|---|---|---|---|---|---|---|
| 3 | 36.3 | 19.53 | 0.59 | 60 | 170 | 135 | 83.4 | 88 |
| 4 | 16.0 | 25.01 | 0.20 | 120 | 170 | 135 | 81.9 | 97 |
| 5 | 36.3 | 25.15 | 0.46 | 60 | 340 | 130 | 85.5 | 98 |
| 6 | 16.0 | 25.56 | 0.20 | 90 | 340 | 130 | 89.1 | 99.5 |

We claim:

1. In a process for the carboalkoxylation of butadiene by reacting in a first step butadiene, carbon monoxide and at least one lower alkyl alcohol which process comprises introducing at least about 0.15 mole of a cobalt-containing catalyst based upon cobalt and at least 0.5 mole of nitrogen base per mole of butadiene along with carbon monoxide, alcohol and butadiene into a reactor and thereafter reacting the butadiene at elevated temperature and pressure to form an alkylpentenoate, followed by a second step comprising the carboalkoxylation of the alkylpentenoate to a dialkyladipate at an increased temperature relative to the first step and wherein essentially no components are removed from the reaction product between the first and second steps.

2. The process of claim 1 wherein 0.17–0.45 mole of cobalt-containing catalyst and 0.5–3 moles of nitrogen base are introduced into the reactor for each mole of butadiene.

3. The process of claim 1 wherein the molar ratio of butadiene to cobalt-containing catalyst to nitrogen base as introduced is in the range 1 to 0.2–0.4 to 1–2.5, respectively.

4. The process of claim 1 wherein the pressure is maintained in the range 100–500 atm.

5. The process of claim 2 wherein the cobalt-containing catalyst is cobalt carbonyl.

6. The process of claim 5 wherein the nitrogen base is pyridine.

7. The process of claim 3 wherein the cobalt-containing catalyst is cobalt carbonyl and the nitrogen base is pyridine.

* * * * *